United States Patent [19]

Saint-Jalmes

[11] Patent Number: 6,166,271
[45] Date of Patent: Dec. 26, 2000

[54] METHOD FOR SYNTHESIS OF HYDROCARBON COMPOUNDS CONTAINING FLUORINE ON AT LEAST ONE ALKYL CHAIN CARBON

[75] Inventor: Laurent Saint-Jalmes, Meyzieu, France

[73] Assignee: Rhodia Chimie, Courbevoie Cedex, France

[21] Appl. No.: 09/180,598

[22] PCT Filed: May 6, 1997

[86] PCT No.: PCT/FR97/00803

§ 371 Date: Jan. 19, 1999

§ 102(e) Date: Jan. 19, 1999

[87] PCT Pub. No.: WO97/43231

PCT Pub. Date: Nov. 20, 1997

[30] Foreign Application Priority Data

May 10, 1996 [FR] France .................................. 96-05859

[51] Int. Cl.$^7$ ...................................................... C07C 25/13
[52] U.S. Cl. .............................................................. 570/145
[58] Field of Search ............................................... 570/145

[56] References Cited

U.S. PATENT DOCUMENTS 3,966,832  6/1976  Lademann et al. ..................... 570/145

FOREIGN PATENT DOCUMENTS 0 005 810  5/1979  European Pat. Off. .

OTHER PUBLICATIONS

Database WPI, Section Ch, Week 8430, Derwent Publications Ltd., London, GB; Class E14, AN 84–185448 XP002022623 & JP 59 104 328 A (Hodogaya Chem Ind KK), Jun. 16, 1984.

J. Org. Chem. (Joceah, 00223263), 79; vol. 44, (22) pp. 3872–81, Univ. Southern California; Inst. Hydrocarbon Chem.; Los Angeles; 90007; CA, USA, XP002022622, Olah G.A. et al, "Synthetic methods and reactions. 63. Pyridinium poly(hydrogen fluoride) 30% pyridine—70% hydrogen fluoride): a convenient reagent for organic fluorination reactions", p. 3878, table XIV (1979).

*Primary Examiner*—Alan Siegel
*Attorney, Agent, or Firm*—Burns, Doane, Swecker & Mathis, L.L.P.

[57] ABSTRACT

The invention features a useful method for the synthesis of fluorinated derivatives. It is characterized in that it comprises at least one step in which a substrate comprising one sp$^3$ hybridizing halogenophore carbon bearing at least two halogens, at least one of which is a halogen of an atomic number higher than that of fluorine, which halogenophore carbon is coupled to at least one weak hybridization atom bearing an unsaturation, is subjected to the action of one reagent comprising at least one defined compound selected among those constituted by the association of one Bronstedt base with a defined number n of hydrofluoric acid, n being at least 3 and at most 20, advantageously 15, preferably 10. This invention is useful in organic synthesis.

20 Claims, No Drawings

METHOD FOR SYNTHESIS OF HYDROCARBON COMPOUNDS CONTAINING FLUORINE ON AT LEAST ONE ALKYL CHAIN CARBON

The present invention relates to a process which is useful for the synthesis of hydrocarbon-based compounds containing fluorine on a carbon of an alkyl chain, by exchange between a halogen of a higher row and fluorine by means of a reagent containing fluorine at least partially in the form of complex salts. The invention relates more particularly to a process for obtaining derivatives containing fluorine on a carbon atom bearing groups containing unsaturation or double bonds.

Fluoro compounds are generally difficult to obtain. The reactivity of fluorine is such that it is difficult, or even impossible, to obtain fluoro derivatives directly.

One of the techniques most commonly used for manufacturing fluoro derivatives consists in reacting a halo, generally a chloro, derivative in order to exchange the halogen with an inorganic fluorine, generally an alkali metal fluoride, in general of high atomic weight.

In general, the fluoride used is potassium fluoride, which constitutes a satisfactory economic compromise.

Under these conditions, many processes such as, for example, those described in Certificate of Addition No. 2,353,516 and in the article Chem. Ind. (1978)—56 have been described and used industrially to obtain aryl fluorides, onto which aryls are grafted electron-withdrawing groups.

Except for the case in which the substrate is particularly suitable for this type of synthesis, this technique has drawbacks, of which the main ones will be analysed below.

The reaction requires reagents, for instance alkali metal fluorides such as potassium fluoride, which are made relatively expensive due to the specifications they must meet in order to be suitable for this type of synthesis; they must be very pure, dry and in a suitable physical form.

In addition, this reaction does not work for an entire class of products, in particular those bearing [lacuna] on the halophoric carbon (i.e. the carbon bearing the halogen(s) intended to be exchanged with fluorine).

Reagents such as hydrofluoric acid in liquid form or diluted with dipolar aprotic solvents are also used. However, hydrofluoric acid is too powerful a reagent and often leads to unwanted polymerization reactions or to tars.

In this case, and in particular when derivatives are desired containing fluorine on a carbon of alkyl type (including aralkyl) which is electron-poor due to the presence of groups of electron-withdrawing type, a person skilled in the art is confronted with an alternative whose terms are hardly encouraging; alternatively, very harsh conditions are selected and tars are especially obtained, or alternatively mild reaction conditions are used and, in the best of cases, the unchanged substrate is recovered. Finally, it should be pointed out that certain authors have proposed carrying out exchanges using hydrofluoric acid salts as reagents in the presence of heavy elements in the form of oxides or fluorides. Among the elements used, mention should be made of antimony and heavy metals such as silver or quicksilver (mercury).

Another problem is the reaction selectivity: when there are several halogens to be exchanged on the same carbon, it is often difficult to exchange only some of them.

Consequently, one of the aims of the present invention is to provide a process which is capable of carrying out exchange between heavy halogens such as chlorine, on the one hand, and fluorine, on the other hand, by significantly improving the reaction specificity.

Another aim of the present invention is to provide a process which is capable of carrying out exchange between heavy halogens such as chlorine, on the one hand, and fluorine, on the other hand, using particularly mild reaction conditions. Another aim of the present invention is to provide a process which uses a source of fluoride whose morphology is less critical.

Another aim of the present invention is to provide a process which exchanges only one halogen atom out of two or three possible ones.

Another aim of the present invention is to provide a process which exchanges only two halogen atoms out of three possible ones.

Another aim of the present invention is to provide a process which exchanges molecules or atoms only if this gives carbon atoms which bear only one fluorine atom concomitantly with one or two other halogens which are different from fluorine.

Another aim of the present invention is to provide a process which exchanges molecules or atoms only if this gives carbon atoms which bear only two fluorine atoms concomitantly with another halogen which is different from fluorine.

Another aim of the present invention is to provide a process which avoids the use of large amounts of metals known to be expensive or toxic, such as mercury and/or silver.

Another aim of the present invention is to provide a process which reduces the amounts of metals known to be expensive or toxic, such as mercury and/or silver, such that the molar ratio between the metal and the substrate whose halogen atoms are to be exchanged is at a value of not more than 0.5, advantageously not more than 0.2, preferably not more than 0.1.

Another aim of the present invention is to provide a process which completely avoids the use of metals known to be expensive or toxic, such as mercury and/or silver, so as not to add any of the abovementioned elements to the reaction mixture; in other words, such that the concentrations of each of the said metals do not exceed values of $10^{-3}$ M; advantageously $10^{-4}$ M, preferably $10^{-5}$ M.

These aims and others which will become apparent later are achieved by means of a process which is useful for the synthesis of fluoro derivatives, this process including the step in which a substrate containing at least one $sp^3$-hybridized halophoric carbon bearing at least two halogens at least one of which is a halogen with an atomic number greater than that of fluorine, which halophoric carbon is connected to at least one atom of low hybridization bearing unsaturation, is subjected to the action of a reagent containing at least one given compound chosen from those consisting of the combination of a Brönstedt base with a given number n of hydrofluoric acid units, n being at least equal to 3 and not more than 20, advantageously not more than 15, preferably not more than 10.

The present invention is not directed towards the case in which the said halophoric carbon bears a chalcogen.

Besides the case in which the said atom of low hybridization bearing unsaturation is engaged in a carbon—carbon bond (acetylenic, preferably ethylenic, this ethylenic bond advantageously being engaged in a ring of aromatic nature), it may be pointed out for instructional purposes, for example, that, advantageously, the said atom of low hybridization bearing unsaturation is an atom engaged in one of the following double bonds [in which *C is the halophoric carbon]:

| Atom of low hybridization and the unsaturation it bears | Degree of ease of exchange reaction (1 = easy; 2 = less easy but more selective; 3 = relatively difficult) | Comments |
| --- | --- | --- |
| —*C—CR"=NR' | 2 | With HF already constitutes an HF base medium [the sequence can even be found in substituted pyridines]* |
| —*C—CR"=S' | 1 | |
| —*C—C=N—NH—R' | 2 | With HF already constitutes an HF base medium* |
| —*C—CR"=N—O—R' | 2 | With HF already constitutes an HF base medium* |
| —*C—CR"=PR' | 2 | With HF already constitutes an HF base medium* |
| —*C—N=NR' | 2 | Compound occasionally fragile, which limits the range of acceptable operating conditions |
| —*C—CF=CF$_2$ | 2 | |
| —*C—CR="O | 3 | Difficult reaction |
| —*C—N=O | 2 | Can give rise to very complex mixtures |

* however, since the reaction is generally carried out with a very large excess of reagent, it is preferable to use a different base in order to produce the excess of reagent (which may or may not correspond to the stoichiometry), especially when a strong reagent is necessary. It is virtually impossible to give the stoichiometry of the exchange reaction; nevertheless, as a guide, if it is taken that each HF base compound exchanges only one fluorine, then it is very desirable to use at least the stoichiometric amount, advantageously at least one and a half times, preferably at least five times and more generally at least 10 times that amount. The upper limit is merely an economic limit of generally about 100 (in the present description, the term "about" is used to emphasize the fact that when the figure(s) furthest to the right in a number is (are) zeros, these zeros are positional zeros rather than significant figures, except, of course, unless otherwise specified).

In formula I relating to the preferred substrates, R" corresponds to $R_{10}$, whereas R' corresponds to $R_5$.

In the course of the study which led to the present invention, it has been shown that certain carbon atoms (defined in the present description as halophoric carbon atoms since they bear a halogen) bearing groups which are electron-withdrawing by means of an inductive effect, with the proviso that at least one of the substituents on the halophoric carbon bore unsaturation which was stable under the operating conditions and that the said halophoric carbon was in an α position, were capable of reacting with a reagent of the above type.

It is recalled that the present invention is not directed towards the case in which the said halophoric carbon bears a chalcogen.

The reaction temperature ranges from the melting point of the reaction mixture to its decomposition or boiling point, in general from 0° C. to 150° C., advantageously from 20 to 100° C.

The process is generally performed at atmospheric pressure, but it is possible to work at pressures which can be up to $20 \times 10^5$ pascals.

Among the preferred bases, mention may be made of those which are hydrocarbon-based trivalent derivatives of the elements from column VB, advantageously from a period at least equal in rank to the second and generally lower than the sixth, of the Periodic Table of the Elements (supplement to the Bulletin de la Société Chimique de France, January 1966, No. 1). Besides those which are detailed below, examples of such compounds which may be given are trivalent derivatives, which, when they are trisubstituted, are in fact pnictines, these pnictines being described in greater detail below.

Among the said hydrocarbon-based derivatives of the elements from column V, the preferred ones are those derived from hydrogen pnictides by total or partial replacement of the hydrogen with hydrocarbon-based residues which can be connected to the atom from column VB via a double bond (as in imines) or a triple bond (as in nitrites).

However, the hydrocarbon-based derivatives of the elements from column V are advantageously derived from hydrogen pnictides by total or partial replacement of the hydrogen with monovalent hydrocarbon-based residues, advantageously with alkyls [in the present description, alkyl is taken in its etymological sense as a hydrocarbon residue of an alkanol after ignoring the alcohol (or -ol) function]; by analogy with the term pnictide, these alkyl compounds will be referred to in the present description as pnictines.

Thus, in the case of nitrogen, substitution of hydrogen nitride (ammonia) gives amines, in the case of phosphorus, substitution of hydrogen phosphide gives phosphines, in the case of arsenic, substitution of hydrogen arsenide gives arsines and in the case of antimony, substitution of hydrogen antimonide (or stibide) gives stibines. They are advantageously chosen from hydrocarbon-based derivatives of phosphorus such as phosphines.

Moreover, the weaker and softer the base, the better and more complete the exchange. Thus, primary, secondary and, preferably, tertiary amines give reagents containing few HF groups (not more than 5, generally fewer) and which are not as strong as the bases of aromatic heterocycle type in which the, or at least one of the, heteroatoms is chosen from column V.

These compounds formed from a base and from a discrete number of HF units will be referred to hereinbelow as "HF base" or "base HF" complex(es).

The present invention is not directed towards exchanges with metal fluorides (in particular alkali metal fluorides such as KF, CsF, etc.), which can be expressed by the fact that the amount [(expressed as equivalents) of cation(s) (alkali metals, ammoniums)] should be at least equal to one times (advantageously at least to 4/3 times, preferably to about twice) that of the hydrogen in the form of free proton, evolved hydrohalic acid or "base HF" complexes, including "F$^-$(HF)" complexes.

The following empirical rule can be given: if the bases form defined compounds containing more than 5 HF per basic function (the prime example of strong reagents is the defined compound pyridine.10HF), then this is a powerful reagent capable of exchanging two heavy halogens on the same carbon under very mild conditions, or even three under slightly harsher conditions (temperature and pressure). Otherwise, it is a more selective reagent which generally exchanges only to give a single fluorine on a carbon under mild conditions and two fluorines on the so-called halophoric carbon under harsher conditions. This invention is especially advantageous for replacing chlorines with fluorines.

Thus, the exchange reactions are essentially successive (since each additional fluorine atom on the halophoric carbon slows down the exchange of halogen atoms heavier than fluorine with the latter), thereby giving a selective or complete exchange, by varying the operating conditions and the choice of reagents. Since it is generally possible to find conditions under which the exchange reaction stops before all of the halogens heavier than fluorine have been replaced by fluorine, it follows that two levels of selectivity are possible. On the one hand, it is possible to exchange only a limited number of the halogens heavier than fluorine, and, on the other hand, it is possible to treat a mixture which is already partially fluorinated and to have a significant effect only on the molecules which have not reached the desired number of fluorine atoms.

In general, the ease of exchange of a halogen atom heavier than fluorine with the latter increases as its atomic number increases.

Obviously, the stoichiometry and its excess can be varied in order to limit the number of halogen atoms exchanged per molecule.

It is possible for there to be several halophoric carbon atoms per molecule. It is preferable for two halophoric atoms not to interfere with each other.

A typical profile of the carbon atoms, or even the molecules, which are most able to exchange their heavy halogens with fluorine under the action of the above reagents will be given below. Each characteristic below makes the value of the invention for the said carbons more obvious.

Thus, it is particularly advantageous for any residual bond on the halophoric carbon advantageously to be a bond with a group chosen from the groups which are electron-withdrawing by means of an inductive effect. The said group chosen from the electron-withdrawing groups is advantageously a halogen.

Thus, it is also particularly advantageous for any residual bond on the halophoric carbon advantageously to be a bond with another atom of low hybridization bearing unsaturation.

The said unsaturation which the said atom of low hybridization bears is advantageously chosen such that addition or polymerization reactions are poorly favoured. Thus, aromatic unsaturation is particularly suitable.

The invention is particularly useful when the said starting halophoric carbon bears at least two halogens of atomic number greater than that of fluorine.

As will be outlined later, the invention is particularly advantageous when the said halophoric carbon is trihalomethyl, i.e. when it bears three halogens advantageously chosen from chlorine and fluorine.

Thus, to summarize the above, even if it is superfluous, it may be mentioned that the substrates can advantageously be molecules of formula I:

$$R—CXX'—Z(R_{10})_r{=}Z'(R_{11})_s{—}(R_5)_t \qquad (I)$$

with R chosen from hydrocarbon-based residues (in particular aryl or alkyl), halogens and electron-withdrawing groups (preferably by means of an inductive effect);

with X and X', which may be identical or different, chosen from halogens, preferably chlorine (with, of course, the condition that R, X and X' cannot simultaneously be fluorine and that one of them represents at least one halogen heavier than fluorine which is to be exchanged with fluorine);

Z is chosen from trivalent metalloids with r equal to zero or tetravalent metalloids with r equal to 1 (respectively phosphorus and, advantageously, nitrogen, on the one hand, and carbon, on the other hand, preferably carbon);

and Z' is chosen from metalloids, advantageously chalcogens (with s and t equal to zero), nitrogen and phosphorus (with s equal to zero) and carbon with s and t equal to 1);

r, s and t can take the values zero or one, depending on what Z and Z' represent. Surprisingly, R can be hydrogen and can give rise to easy exchange especially when the compound is of formula II, preferably when Ar is homocyclic.

R can also be of the type $—Z(R_{10})_r{=}Z'(R_{11})_s{—}(R_5)_t$, including the type $Ar(R_{11})_s$, which may or may not give a symmetrical molecule.

$R_5$ can be hydrogen or any radical, advantageously a hydrocarbon-based radical (i.e. one containing carbon and hydrogen).

$R_{10}$ can independently take the same values as $R_s$.
$R_{11}$ can independently take the same values as $R_5$.

However, according to the present invention, $R_{10}$ and $R_5$ are advantageously linked to form an aromatic ring, which then implies that Z is carbon.

Formula (I) then becomes $$R—CXX'—Ar(R_{11})_s \qquad \text{(Formula II)}$$

where Ar represents an optionally substituted aromatic ring. It represents in particular an optionally substituted benzenic ring (such as a phenyl or a naphthyl) or an optionally substituted heterocycle, $R_{11}$ then representing the optional substituent ortho to the halophoric carbon (CXX').

The compounds in which Ar is five-membered, preferably with two heteroatoms (it is desirable to have two nitrogen atoms), are of particular value.

When $Z(R_{10})_r{=}Z'(R_{11})_s{—}(R_5)_t$ is electron-withdrawing (as in the case of the six-membered heterocycles such as pyridine), it should be noted that the exchange is more difficult, especially for the third fluorine atom on the same carbon. This is particularly advantageous in the case of a partial selective exchange.

Each radical R and $R_5$, $R_{10}$ and $R_{11}$ usually contains not more than 30 (including not more than 20 carbon atoms), advantageously 20 (including not more than 15 carbon atoms) and preferably 15 carbon and/or nitrogen atoms (including not more than 12 carbon atoms). The total number of carbons in the substrate molecules rarely exceeds 50 and is advantageously not more than 30.

$R_5$ represents an optionally substituted phenyl ring, an optionally substituted heterocycle, advantageously a five-membered heterocycle, preferably containing two heteroatoms (it is desirable to have two nitrogen atoms).

The term electron-donating or weakly electron-withdrawing should be understood to mean a group which is as withdrawing as or less withdrawing than a dichlorophenyl (this definition also being suitable for non-electron-withdrawing aryl or for an electron-rich aryl radical). The opposite case gives the definitions "electron-withdrawing" or "significantly electron-withdrawing".

To assist those skilled in the art to determine the conditions to be selected depending on the case encountered, empirical rules which can be used in most situations encountered will be found below.

If it is desired to carry out complete exchanges, it is desirable to use strong reagents under harsh or very harsh conditions. Conversely, weak reagents under mild conditions lead to very selective exchanges, in general to monoexchanges (leading to products which are monofluorinated on the halophoric carbon). A weak reagent and harsh conditions or a strong reagent and mild conditions generally give intermediate results.

These rules should be modified on the basis of the ability of the substrates to be substituted. The more donating the nature of the substituents on the halophoric carbon, the greater the ease of exchange of the substrate (i.e. the easier it is to reach the final number of fluorines on the halophoric carbon).

The prime example of weak reagents is the compound defined as triethylamine.3HF.

The prime example of strong reagents is the compound defined as pyridine.10HF. mild conditions:

θ=melting point to not more than 50° C.;

harsh conditions: 50° C. to 100° C. (or to the boiling point if this is lower at the pressure considered); very harsh conditions:

θ=100 to 150° C.

and, where appropriate, pressures above atmospheric pressure; the selectivity arises from the fact that by using the reagents of the present invention, the exchanges are successive and the more fluorines there are on the halophoric carbon, the more difficult and slower the reaction.

In the case where, in formula (I), X and X' represent halogens heavier than fluorine, the details of the reaction equations can be given—reaction giving one fluorine on the halophoric carbon:

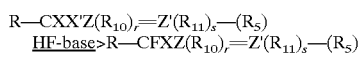
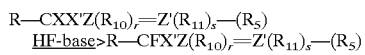

reactions giving two fluorines on the halophoric carbon:

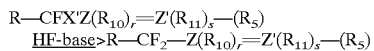

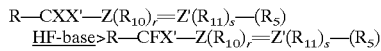

And, with R representing a halogen heavier than fluorine—reactions giving three fluorines on the halophoric carbon:

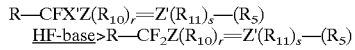

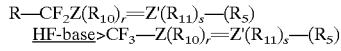

The non-limiting examples which follow illustrate the invention.

Preparation of HF-Base Solutions—General Procedure

The various HF-base media are synthesized as follows:

Y mol of anhydrous hydrofluoric acid are added dropwise to x mol of an organic base (pyridine, triethylamine, dioxane, etc.) or inorganic base (KF, BU$_4$NF, etc.) with stirring (optionally cooled to −20° C.). After addition of the anhydrous hydrofluoric acid, the reaction medium is heated to room temperature and used without any processing. The HF-base complex thus has the structure (HF)$_y$-base$_x$.

After the reaction, when the fluorination crude product is treated with an anhydrous organic phase which is immiscible with the HF-base medium considered, but capable of dissolving the product formed (for example only CH$_2$Cl$_2$ (without ice or water)), two phases are obtained: the less polar phase (for example CH$_2$Cl$_2$) which contains the product obtained after exchange, and the more polar phase "HF-base" which can then be recycled, after optionally returning to the initial titre (of HF) and removal of the hydrohalic acid evolved by the reaction (for example by distillation). This recycling is an intrinsic feature of the process according to the present invention and is an additional advantage of the process.

EXAMPLE NO. 1

Cl/F Exchange Starting With Trichloromethylbenzene

1a) Exchange of a Chlorine Atom

Reaction equation

Procedure used:

1.95 g (0.01 mol) of trichloromethylbenzene are added to 21 g (0.13 mol) of [HF]$_3$-triethylamine complex at 20° C.

The reaction medium is then heated and stirred at 70° C. for 10 h.

The crude reaction product is then poured onto a mixture of CH$_2$Cl$_2$ (200 ml) and ice (200 g).

The organic phase is washed 4 times with 50 ml of water and dried over magnesium sulphate. The solvent (CH$_2$Cl$_2$) is evaporated off, the residue is analysed by gas chromatography and the products formed are identified by $^{19}$F NMR.

A mixture of 2 products is thus obtained:

The degree of conversion of the trichloromethylbenzene is 100%.

A mono-exchange of chlorine is thus achieved under these reaction conditions.

1b) Exchange of 2 Chlorine Atoms

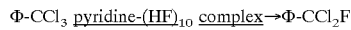

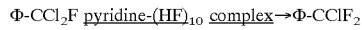

Procedure used 1.95 g (0.01 mol) of trichloromethylbenzene is added to 11.2 g (0.04 mol) of [HF]$_{10}$-pyridine complex 1 (prepared from 77.3 g of pyridine and 200 g of anhydrous hydrofluoric acid) cooled to 0° C.

The reaction medium is then warmed to room temperature and stirred for 2 h.

The crude reaction product is then poured onto a mixture of CH$_2$Cl$_2$ (200 ml) and ice (200 g).

The organic phase is washed 4 times with 100 ml of water and dried over magnesium sulphate. The solvent (CH$_2$Cl$_2$) is evaporated off to give an oil which is analysed by gas chromatography, the structure of the products being obtained by $^{19}$F NMR.

A mixture of 2 products is thus obtained:

The degree of conversion of the trichloromethylbenzene is 100%.

A double-exchange is thus achieved under these reaction conditions.

1c) Exchange of Three Chlorine Atoms

Reaction equations

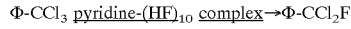

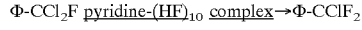

Procedure used 1.95 g (0.01 mol) of trichloromethylbenzene is added to 11.2 g (0.04 mol) of [HF]$_{10}$-pyridine complex 1

(prepared from 77.3 g of pyridine and 200 g of anhydrous hydrofluoric acid) cooled to 0° C.

The reaction medium is then heated at 50° C. and stirred for 24 hours.

The crude reaction product is then poured onto a mixture of $CH_2Cl_2$ (200 ml) and ice (200 g).

The organic phase is washed 4 times with 100 ml of water and dried over magnesium sulphate. The solvent ($CH_2Cl_2$) is evaporated off to give an oil which is analysed by gas chromatography, the structure of the products being obtained by $^{19}F$ NMR.

A mixture of 2 products is thus obtained:

Φ-$CClF_2$ 15%

Φ-$CF_3$ 84%

The degree of conversion of the trichloromethylbenzene is 100%.

A triple-exchange is thus predominantly achieved under these reaction conditions.

The results obtained using trichloromethylbenzene are collated in the following table.

| HF-base medium used | Duration | Temperature | Φ-$CCl_3$ | Φ-$CCl_2F$ | Φ-$CClF_2$ | Φ-$CF_3$ |
|---|---|---|---|---|---|---|
| [HF]$_3$-triethylamine | 10 h00 | 70° C. | — | 86% | 8% | 0% |
| [HF]$_{10}$-pyridine 1 | 2 h00 | 25° C. | — | — | 92% | 8% |
| [HF]$_{10}$-pyridine 1 | 24 h00 | 50° C. | — | — | 15% | 84% |

EXAMPLE NO. 2

Cl-F Exchange Using Dichloromethylbenzene

2a) Exchange of a Chlorine Atom

Reaction equation

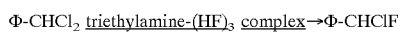

Φ-$CHCl_2$ triethylamine-(HF)$_3$ complex→Φ-$CHClF$

Procedure used:

0.35 g (2.17 mmol) of dichloromethylbenzene is added to 4.6 g (0.03 mol) of [HF]$_3$-triethylamine complex at 20° C.

The reaction medium is then heated and stirred at 70° C. for 14 h.

The crude reaction product is then poured onto a mixture of $CH_2Cl_2$ (50 ml) and ice (50 g).

The organic phase is washed 4 times with 20 ml of water and dried over magnesium sulphate. The solvent ($CH_2Cl_2$) is evaporated off, the residue is analysed by gas chromatography and structures of the products formed are identified by $^{19}F$ NMR.

The compound Φ-CHClF is thus predominantly obtained with a selectivity of about 40%.

The degree of conversion of the dichloromethylbenzene is 50%.

2b) Exchange of 2 Chlorine Atoms

Reaction equations

Φ-$CHCl_2$ pyridine-(HF)$_{10}$ complex→Φ-CHCl

Φ-CHClF pyridine-(HF)$_{10}$ complex→Φ-$CHF_2$

Procedure used:

1.6 g (0.01 mol) of dichloromethylbenzene is added to 11.2 g (0.04 mol) of [HF]$_{10}$-pyridine complex 1 (prepared from 77.3 g of pyridine and 200 g of anhydrous hydrofluoric acid) cooled to 0° C.

The reaction medium is then stirred at 25° C. for 14 h.

The crude reaction product is then poured onto a mixture of $CH_2Cl_2$ (200 ml) and ice (150 g).

The organic phase is washed 4 times with 50 ml of water and dried over magnesium sulphate. The solvent ($CH_2Cl_2$) is evaporated off, the residue is analysed by gas chromatography and the structures of the products formed are identified by $^{19}F$ NMR.

The compound Φ-$CHF_2$ is thus predominantly obtained with a selectivity of about 70%.

The degree of conversion of the dichloromethylbenzene is 100%.

What is claimed is:

1. Process for the synthesis of fluoro derivatives, comprising subjecting a substrate to the action of a reagent, wherein the substrate comprises at least one $sp^3$-hybridized halophoric carbon bearing at least two halogens at least one of which is a halogen with an atomic number greater than that of fluorine, wherein the halophoric carbon is connected to at least one atom of low hybridization bearing unsaturation, and wherein the reagent comprises the combination of a Brönstedt base with a given number n of hydrofluoric acid units, n being at least equal to 3 and not more than 20, and wherein the halophoric carbon does not bear a chalcogen.

2. Process according to claim 1, wherein any residual bond on the halophoric carbon is bonded with a group chosen from groups which are electron-withdrawing by means of an inductive effect, and from aryl groups.

3. Process according to claim 1, wherein said atom of low-hybridization bearing unsaturation is an $sp^2$-hybridized carbon atom.

4. Process according to claim 1, wherein said group is a halogen.

5. Process according to claim 1, wherein said halophoric carbon bears at least two halogens of atomic number greater than that of fluorine.

6. Process according to claim 1, wherein said halophoric carbon bears three halogens chosen from chlorine and fluorine.

7. Process according to claim 1, wherein said atom of low hybridization bearing unsaturation belongs to an aromatic ring.

8. Process according to claim 1, wherein said atom of low hybridization bearing unsaturation belongs to an electron-rich aromatic ring or one which is not particularly electron-poor.

9. Process according to claim 1, wherein said atom of low hybridization bearing unsaturation belongs to an aromatic ring containing heteroatoms.

10. Process according to claim 1, wherein said atom of low hybridization bearing unsaturation belongs to a five- or six-membered aromatic ring.

11. Process according to claim 1, wherein said atom of low hybridization bearing unsaturation belongs to an aromatic ring containing five other carbon ring-members, which are themselves optionally substituted.

12. The process according to claim 1, wherein n is not greater than 15.

13. The process according to claim 12, wherein n is not greater than 10.

14. The process according to claim 1, wherein the halophoric carbon bears two or three halogens, and wherein one of the halogens is replaced by a fluorine atom as a result of subjecting the substrate to the action of the reagent.

15. The process according to claim 1, wherein the halophoric carbon bears three halogens, and wherein two of the halogens are replaced by fluorine atoms as a result of subjecting the substrate to the action of the reagent.

16. Process for the synthesis of fluoro derivatives, comprising subjecting a substrate to the action of a reagent only if an $sp^3$-hybridized halophoric carbon atom of the substrate is produced which bears only one fluorine atom and one or two halogens other than fluorine, wherein the substrate comprises the $sp^3$-hybridized halophoric carbon bearing at least two halogens at least one of which is a halogen with an atomic number greater than that of fluorine, wherein the halophoric carbon is connected to at least one atom of low hybridization bearing unsaturation, and wherein the reagent comprises the combination of a Brönstedt base with a given number n of hydrofluoric acid units, n being at least equal to 3 and not more than 20, and wherein the halophoric carbon does not bear a chalcogen.

17. Process for the synthesis of fluoro derivatives, comprising subjecting a substrate to the action of a reagent only if an $sp^3$-hybridized halophoric carbon atom of the substrate is produced which bears only two fluorine atoms and one halogen other than fluorine, wherein the substrate comprises the $sp^3$-hybridized halophoric carbon bearing at least two halogens at least one of which is a halogen with an atomic number greater than that of fluorine, wherein the halophoric carbon is connected to at least one atom of low hybridization bearing unsaturation, and wherein the reagent comprises the combination of a Brönstedt base with a given number n of hydrofluoric acid units, n being at least equal to 3 and not more than 20, and wherein the halophoric carbon does not bear a chalcogen.

18. The process according to claim 1, wherein the substrate is subjected to the action of the reagent in the presence of a heavy metal, and wherein the molar ratio of the heavy metal to the substrate is not more than 0.5.

19. The process according to claim 18, wherein the substrate is subjected to the action of the reagent in the presence of a heavy metal, and wherein the molar ratio of the heavy metal to the substrate is not more than 0.2.

20. The process according to claim 19, wherein the substrate is subjected to the action of the reagent in the presence of a heavy metal, and wherein the molar ratio of the heavy metal to the substrate is not more than 0.1.

* * * * *